United States Patent [19]

Ellett

[11] 4,391,152

[45] Jul. 5, 1983

[54] SAMPLER

[75] Inventor: James R. Ellett, Edmonton, Canada

[73] Assignee: Bralorne Resources Limited, Vancouver, Canada

[21] Appl. No.: 267,856

[22] Filed: May 28, 1981

[30] Foreign Application Priority Data

Dec. 16, 1980 [CA] Canada .................................. 366918

[51] Int. Cl.³ .............................................. G01N 1/14
[52] U.S. Cl. ................................................ 73/863.84
[58] Field of Search ........... 73/863.83, 863.84, 864.34, 73/864.35; 251/213, 279

[56] References Cited

U.S. PATENT DOCUMENTS

| 2,548,193 | 4/1951 | Blum | 73/863.84 |
| 2,986,940 | 6/1961 | Russell | 73/863.83 |
| 3,058,351 | 10/1962 | McFarland et al. | 73/864.84 |
| 3,238,784 | 3/1966 | Dorsey et al. | 73/863.85 |
| 3,442,136 | 5/1969 | Wilson | 73/864.34 |
| 3,848,470 | 11/1974 | Hargash et al. | 73/864.34 |

Primary Examiner—S. Clement Swisher
Attorney, Agent, or Firm—Wenderoth, Lind & Ponack

[57] ABSTRACT

A sampling device for sampling fluids such as those carried in an oil pipeline comprises two valve means and a sampling chamber located on the fluid passageway in the sampler housing. Fluid is admitted to the probe of the sampling device when the first valve means allows the passageway to be opened and the fluid is admitted or drawn into the sampling chamber. After the first valve means is closed, the second valve means is opened and the fluid exits from the sampling chamber under the action of the plunger. Provision is made to easily clean the buildup of deposits in the fluid passageway without disassembly of the sampling device.

29 Claims, 3 Drawing Figures

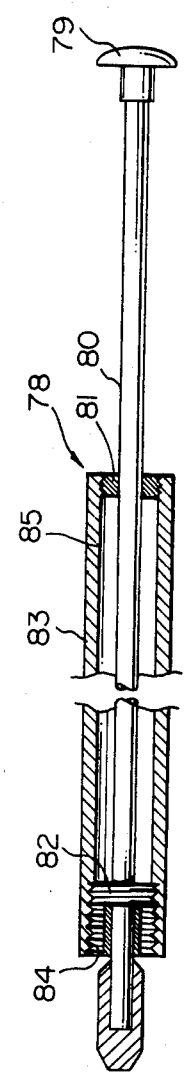
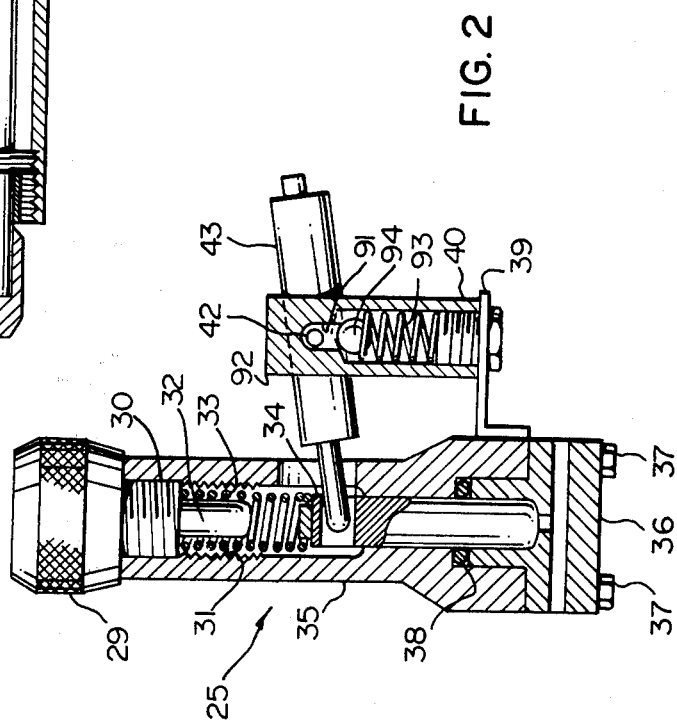
FIG. 3
FIG. 2

SAMPLER

INTRODUCTION

This invention relates to a fluid sampling device and, in particular, to a sampling device used on oil pipelines.

BACKGROUND OF THE INVENTION

Sampling devices or "samplers" are commonly used in oil production when custody of the oil changes. They receive or extract a representative sample of the oil being transferred, such as that oil flowing in a pipeline. Subsequent laboratory analysis of the samples taken by the "sampler" reveals the percentages of wax, basic sediment and water in the oil.

Prior devices used for sampling have suffered from various problems. They may consist of valves used to allow the admission and exit of oil through a passageway from the vessel being sampled and this passageway can become clogged with foreign material in the oil including wax. Disassembly of the sampler for cleaning purposes may be necessitated by the deposit of the foreign substance in the passageway.

A further problem associated with prior devices is that whereas sampling is ordinarily taken automatically, it may be desired to manually rotate the valves to obtain a fluid sample. Disassembly of the sampler may again be necessary and, upon reassembly, the timing sequence of the valve operation used in automatic sampling may need readjustment.

Yet a further problem associated with pior samplers relates to the removal of the sampler from the pipeline or vessel containing the fluid to be sampled. Removal of the sampler may be desired for purposes of repair or maintenance and to accomplish the removal, tedious precautions may be necessary when removing the sampler including, in some instances, the necessity for temporarily shutting down the pipeline.

Finally, previous samplers may be designed to operate completely only under certain pressure limits of the fluid in the pipeline. If the pressure is too low, the operation of the sampler is no longer effective. Accordingly, it is desirable for a sampler to operate without regard to the minimum pressure in the pipeline or fluid carrying vessel.

SUMMARY OF THE INVENTION

In accordance with one aspect of the invention, there is disclosed a sampling device for taking fluid samples, said device comprising a probe adapted to extend into fluid and to act as an intake port, a housing connected to said probe, first valve means in said housing adapted to allow admittance of a portion of said fluid, second valve means adapted to allow exit of said admitted fluid to a storage container, sample holding means adapted to hold a predetermined amount of said admitted fluid, actuating means adapted to open and close said first and second valve means at predetermined intervals to allow for said admittance and exit of said fluid, respectively, and a substantially uninterrupted passageway for said fluid extending through said housing and probe, said passageway being adapted to allow for the admission of cleaning means to clean said passageway without disassembly of said probe and housing.

In accordance with a further aspect of the invention, there is disclosed a sampling device for sampling fluid, said device comprising a probe, a housing connected to said probe, a passageway extending through said probe and housing, first and second valve means and a sampling chamber in said housing adapted to receive fluid when said first valve means is opened and to allow said fluid to exit when said second valve means is opened and said first valve means is closed, and actuating means connected to said housing for a sequential operation cycle of opening and closing said first and second valve means, said actuating means including coupling means between said actuating means and said first and second valve means, said coupling means allowing manual operation of said first and second valve means without removal of said actuating means from said housing and without destruction of said sequential operation cycle.

In accordance with yet a further aspect of the invention, there is disclosed a sampling device for taking fluid samples, said device comprising a probe adapted to extend into fluid and to act as an intake port, a housing connected to said probe, first valve means in said housing adapted to allow admittance of a portion of said fluid, second valve means in said housing adapted to allow exit of a portion of said fluid to a storage container, sample holding means between said first and second valve means and plunger means in sealing contact with and operable by timed cam means between predetermined limits in said sample holding means independently of the pressure of said fluid.

BRIEF DESCRIPTION OF THE SEVERAL VIEWS OF THE DRAWINGS

An embodiment of the invention will now be described, by way of example only, with reference to the accompanying drawings in which:

FIG. 2 is a sectional view of the trunnion which supports the plunger actuator; and FIG. 3 is a sectional view of the cleaner rod and its stuffing box.

DESCRIPTION OF SPECIFIC EMBODIMENT

Figure 1:
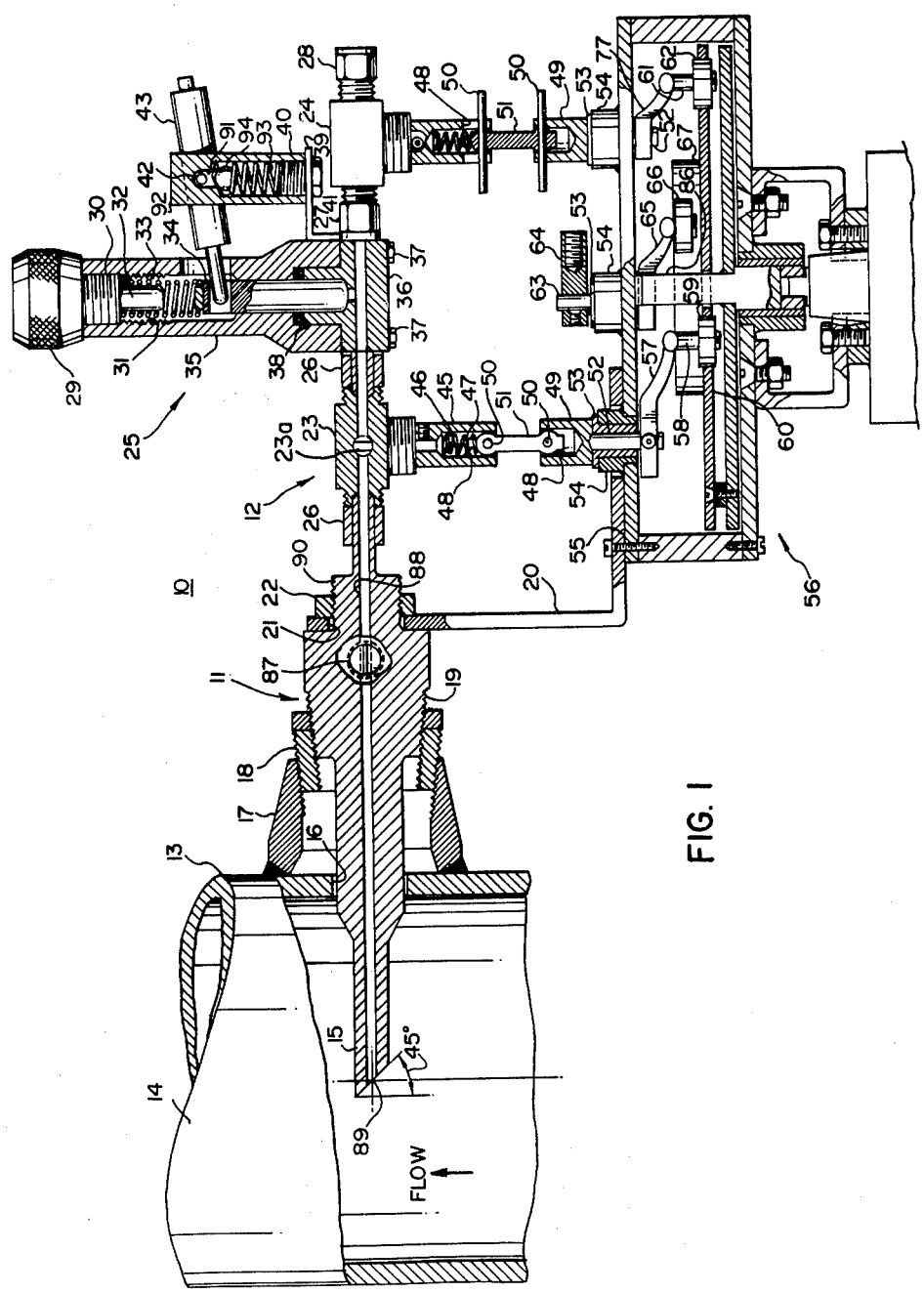
FIG. 1 is a cutaway view of an embodiment of the sampler according to the present invention.

Referring now to FIG. 1, the sampler 10 comprises a probe 11 and a housing 12. Probe 11 extends through the bore 16, drilled in wall 13 of the pipeline 14 and one end 15 of probe 11 acts as an input port for the fluid in the pipeline 14. When properly positioned in the pipeline, the center line of the probe passageway at the tip of the probe 11 will intersect the center line of the pipeline 14 as at 89. The end 15 of probe 11 is bevelled at an angle of 45° as shown and the open port 89 is exposed to the flow is indicated.

An internally threaded boss 17 is connected to wall 13 by welding as shown and reducing bushing 18 is threaded into the thread-o-let 17, the reducing bushing 18 having threads on the inside into which probe 11 is screwed by threaded diameter 19 located on the end of the probe 11 opposite port 89.

A passageway 88 extends through the probe 11 and the housing 12. The diameter of the passageway 88 has been chosen to be a size which will prevent segregation of fluids of different specific gravities while they are resident in the passageway 88 between sample takings which would, if so happening, cause unreliable sample taking. The size of the passageway 88, therefore, is approximately 3/16" in diameter. An internal plug valve 87 extends outwardly beyond the probe 11 and may be manually rotated to close or open the passageway 88.

Housing bracket 20 has a bore 21 which is positioned around threaded diameter 90 of probe 11. A jamb nut 22 is screwed over threaded diameter 90 and tight up against housing bracket 20 thus holding it firmly to the probe 11.

The housing 12 of the sampler 10 also includes a first ball valve 23, a second ball valve 24 and a sampling chamber shown generally at 25. First ball valve 23 is connected by sealing nuts 26 on the end of probe 11 and the inlet of sampling chamber 25, respectively. Second ball valve means 24 is connected on the input end to the outlet of sampling chamber 25 by sealing nut 27 and on the outlet end by sealing nut 28. Sealing nut 28 is adapted to allow exit of the fluid which, after it so exits, is retained by a storage container (not shown).

Sampling chamber 25, as earlier described, is connected between first ball valve 23 and second ball valve 24 and includes top housing 35 and lower body 36. An adjusting knob 29 has a threaded diameter 30 which can be longitudinally adjusted along the axis of the sampling chamber 25 by rotating the adjusting knob 29 which allows threaded diameter 30 to move in and out by means of the complementary threading 31 on the inside of the sampling chamber 25. A protuberance 32 extends from the end of threaded diameter 30 and this protuberance 32 acts as a keeper for internal spring 33. The other end of internal spring 33 contacts plunger 34 which is movable along the longitudinal axis of the sampling chamber 25. Top housing 35 mates with lower body 36 by using four bolts 37, only two of which are shown.

A trunnion bracket 39 is mounted to the outside of top housing 35 and a trunnion 40 is mounted to bracket 39 by bolt 41. Referring to FIG. 2, a trunnion pin 42 is mounted in recess 91 of the two separated arms 92 of the trunnion 40. The trunnion pin 42 extends through plunger actuator 43 and can move upwardly and downwardly within the recess 91. A compression spring 93 is located within the trunnion 40 and acts on ball 94. Ball 94 exerts a force against plunger actuator 43 thus tending to keep trunnion pin 42 in contact with the closed end of the recess 91. One end of plunger actuator 43 engages with plunger 34 as shown and the opposite end engages with a simple adjustable ball joint linkage (not shown) connected between this end and linkage arm 64.

First and second ball valves 23, 24 are identical and, in FIG. 1, first ball valve 23 is shown in the closed position and second ball valve 24 is shown opened. Since the operation of each of the ball valves 23, 24 is similar, only the hardware associated with first ball valve 23 will be described.

A ball valve adaptor 45 extends outwardly from the first ball valve 23 and is connected to the shutter or ball 23a of the first ball valve 23. The ball and, accordingly, ball valve adaptor 45 are adapted to rotate through 90° and, when so doing, the first ball valve 23 moves from an open to a closed position. A cavity 46 within the ball valve adaptor 45 acts as a seat for compression spring 47. Grooves 48 in the ball valve adaptor 45 and in lever and swivel adaptor 49 accommodate roll pins 50. Roll pins 50 extend through swivel linkage 51 within the grooves 48 and the top roll pin 50 acts as a keeper for the compression spring 47.

Lever and swivel adaptor 49 has a shaft 52 connected thereto and shaft 52 rotates within and extends through bushing 53. Bushing 53 is, in turn, mounted within bushing sleeve 54.

Bushing sleeve 54 is mounted on the outer housing 55 of the actuating means shown generally at 56. Shaft 52 has lever 57 connected rigidly thereto and a roller extension 58 has a cam roller 59 mounted thereon for relative rotation. Cam roller 59 rotates in contact with cam 60 under the influence of a spring (not shown).

The second ball valve 24 has identical apparatus extending downwardly and into the actuating means 56. Shaft 52 has lever 77 attached thereto and roller extension 61 has cam roller 62 mounted thereon and rotating in contact with cam 60, again under the influence of a spring (not shown).

A further shaft 63 extends into the actuating mechanism 56 through bushing 53 and bushing sleeve 54. Shaft 63 is connected to linkage arm 64 at one end and at the other end to lever 65. Lever 65 retains cam roller 66 which rotates in contact with cam 67, again under the influence of a spring (not shown).

The working of the actuating means 56 which is used to intermittently energize a motor (not shown) to rotate the cams 60, 67 at predetermined intervals and thereby actuate the ball valves 23, 24 and the plunger actuator 43 is known in the art and forms no part of the present invention. Its details, therefore, will not be further described.

The cleaning rod is shown generally at 78 in FIG. 3. It includes a handle 79 attached to cylindrical shaft 80. Shaft 80 extends through first and second bushings 81, 82, respectively, each bushing having a threaded outside diameter which fits complementary threads formed on the inside diameter of cylinder 83. The threaded inside diameter 84 is adapted to also complement the threads of the fitting of second ball valve 24 when the sealing exit nut 28 is removed and may, therefore, be mounted thereon. A nubbin 95 which is slightly smaller in diameter than the diameter of passageway 88 is permanently mounted on the end of shaft 80. It is bevelled at the forward end at a 15° angle as shown.

OPERATION

In operation, it is assumed the sampler 10 is in the operating position shown in FIG. 1. The timer (not shown) of the actuating means 56 actuates the motor (not shown) and shaft 86 commences to rotate thereby rotating cams 60, 67 relative to cam rollers 59, 62, 66. Cam roller 59 rotates lever 57 and shaft 52. The shaft rotation is transmitted to lever and swivel adaptor 49, thence to the bottom roll pin 50 through swivel linkage 51 to top roll pin 50 and to ball valve adaptor 45. Ball valve adaptor 45 rotates and opens first ball valve means 23.

At approximately the same time, cam roller 66 moves on cam 67 and the rotation of lever 65 is transmitted to shaft 63 and linkage arm 64. Linkage arm 64 transmits this motion through the metering chamber linkage (not shown) to plunger actuator 43 which rotates downwardly about trunnion pin 42 thereby lifting plunger 34 and creating the appropriate volume in sampling chamber 25. Since first ball valve 23 is open, the fluid will flow into and fill the sampling chamber 25 if it is under pressure. If, however, there is no such pressure, the increase in volume of the sampling chamber 25 caused by the movement of the plunger 34 will create a negative pressure thereby drawing fluid into the sampling chamber 25.

At an appropriate interval, after the sampling chamber 25 is full of fluid, first ball valve 23 is closed by the rotation of cam 60 and, in an identical sequence to that of the action of the first ball valve 23, second ball valve 24 is opened. Likewise, plunger 34 of the sampling chamber 25 is moved downwardly thereby forcing the fluid out of the sampling chamber 25 and out through second ball valve 24 when the sealing exit nut 28 has been removed where the fluid may be stored in an appropriate container (not shown). Subsequently, the second ball valve 24 closes, the cams 60, 67 return to their initial position and the sampler 10 awaits the next signal from the timer which initiates the operation of the motor.

Both first ball valve 23 and second ball valve 24 may be manually operated. If it is desired to open or close either valve manually, the swivel linkage 51 is grasped and moved outwardly from lever and swivel adaptor 49 until the bottom roll pin 50 clears the groove 48 whereupon it may be manually rotated relative to the lever and swivel adaptor 49. In that position, the roll pin 50 will be resting under the influence of compression spring 47 on the surface or upper face of lever and swivel adaptor 49. Accordingly, if the actuating means 56 initiates rotation of shaft 86 and, likewise, lever and swivel adaptor 49, the roll pin 50 will drop into groove 48 and the timing cycle of the sampler will automatically be restored. The operation of the second ball valve 24 is identical in respect of manual operation, and, accordingly, will not be further described. It should be explained, however, that internal plug valve 87 will ordinarily be closed before first and second ball valves 24 are manually opened.

If it is desired to clean the passageway 88, internal plug valve 87 is closed and sealing exit nut 28 is removed to allow any fluid within the sampling unit 10 to escape. The cleaning rod 78 is mounted to the second ball valve connection in place of the sealing exit nut 28 by using the threaded connection 84 of cylinder 83. Internal plug valve 87 is then opened as well as first and second ball valves 23, 24 and the shaft 80 with nubbin 95 may be manually operated inwardly and outwardly to remove any debris or wax buildup deposited in the passageway 88. Following the cleaning, cylinder 83 and cleaning rod 78 are removed from the fitting after again closing internal plug valve 87 and sealing exit nut 28 is re-connected to the threaded outlet of second ball valve 24.

If it is desired to change the quantity of fluid sample taken each sample period and with reference to FIG. 2, adjusting knob 29 may be rotated so that protuberance 32 contacts plunger 34 at a desired position which will determine the fluid quantity. It should be noted that the minimum quantity position reached by plunger 34 (that is, the lowermost position in FIG. 2) will always remain the same and the piston 34 will always be positively displaced from this minimum position by the plunger actuator 43. When, however, adjusting knob 29 is moved downwardly, the top of plunger 34 will contact protuberance 33 sooner than under operating conditions where a larger fluid sample is required. In this event, trunnion pin 42 will exert a force on ball 94 and spring 93 which will give and allow trunnion pin 42 to move within recess 91. This movement within recess 91 allows the volume of the sampling chamber 25 to be varied without further adjustments.

If it is desired to remove the housing 12 from the probe 11 for repair or reconditioning or, perhaps, because the sampler 10 is no longer needed at a particular location, the internal plug valve 87 is closed and jamb nut 22 is removed as well as nut 26. All of the sampler 10, except the probe 11, may then be removed without the necessity of sealing the bore in the pipeline or shutting off the pipeline flow.

There has been disclosed a specific embodiment of the device according to the invention. Many changes may be made in the apparatus without departing from the scope of the invention which should, therefore, be limited only by the accompanying claims.

I claim:

1. A sampling device for taking fluid samples, said device comprising a probe adapted to extend into fluid and to act as an intake port, a housing connected to said probe, first valve means in said housing adapted to allow admittance of a portion of said fluid, second valve means adapted to allow exit of said admitted fluid to a storage container, sample holding means adapted to hold a predetermined amount of said admitted fluid, actuating means adapted to open and close said first and second valve means at predetermined intervals to allow for said admittance and exit of said fluid, respectively, and a substantially uninterrupted passageway for said fluid extending through said housing and probe, said passageway being adapted to allow for the admission of cleaning means to clean said passageway without disassembly of said probe and housing.

2. A sampling device as in claim 1 wherein said passageway is substantially longitudinal.

3. A sampling device as in claim 2 wherein said passageway is adapted to admit a substantially rod-shaped cleaner.

4. A sampling device as in claim 3 wherein said rod-shaped cleaner is substantially longitudinal.

5. A sampling device as in claim 2 wherein said samle holding means is adapted to hold said predetermined amount of said admitted fluid after closure of said first valve means and to allow said predetermined amount to exit to said storage container after said second valve means is opened.

6. A sampling device as in claim 5 wherein said actuating means includes cam means.

7. A sampling device as in claim 6 wherein said cam means is connected to said first and second valve means and is adapted to open and close said first and second valve means at said predetermined intervals.

8. A sampling device as in claim 5 wherein said sample holding means is adapted to allow variation of the quantity of said predetermined amount of said admitted pipeline fluid.

9. A sampling device for taking fluid samples, said device comprising a probe adapted to extend into a fluid carrying vessel and to act as an intake port, a housing connected to said probe, first valve means in said housing adapted to allow admittance of said fluid sample, second valve means adapted to allow exit of said admitted fluid to a storage container, sample holding means adapted to hold a predetermined amount of said admitted fluid after closure of said first valve means and to allow exit of said predetermined amount after said second valve means is opened, said sample quantity of said predetermined amount, actuating means including timing means adapted to open and close said first and second valve means at predetermined intervals to allow for said admittance and exit of said fluid, respectively, and a substantially uninterrupted passageway extending through said housing and probe, said passageway being adapted to allow for admission of a rod-shaped cleaner without disassembly of said housing and probe.

10. A sampling device as in claim 9 wherein said passageway and said cleaner are substantially longitudinal.

11. A sampling device for taking fluid samples, said device comprising a probe adapted to extend into fluid and to act as an intake port, a housing connected to said probe, first valve means in said housing adapted to allow admittance of a portion of said fluid, second valve means in said housing adapted to allow exit of a portion of said fluid to a storage container, sample holding means between said first and second valve means and plunger means in sealing contact with and operable by timed cam means between predetermined limits in said sample holding means independently of the pressure of said fluid.

12. A sampling device as in claim 11 wherein said volume of said sample holding means is adjustable to vary the quantity of said predetermined amount of said fluid.

13. A sampling device as in claim 12 wherein said sample holding means is adapted to admit said fluid after opening of said first valve means and to allow exit of said fluid after opening of said second valve means and closure of said first valve means.

14. A sampling device as in claim 13 and further comprising actuating means adapted to open and close said first and second valve means and to allow for the admission and exit of said fluid from said sample holding means.

15. A sampling device as in claim 14 wherein said cam means is operable to open and close said first and second valve means.

16. A sampling device as in claim 15 and further comprising plunger limiting means to restrict the movement of said plunger within said cylinder.

17. A sampling device as in claim 16 wherein said plunger limiting means comprises an adjustable knob having a protuberance extending into said cylinder and is operable upon rotation of said knob to determine said movement of said plunger.

18. A sampling device for sampling fluids, said device comprising a probe adapted to extend into fluid and acting as an input, a housing connected to said probe, first valve means and second valve means within said housing and a sampling chamber having a variable volume, said volume adapted to increase by the action of a plunger oprable in a sealing relationship within said sampling chamber between predetermined limits by cam and follower means independently of the pressure of said fluid, said plunger acting to create a pressure lower than the pressure in said fluid and to allow said fluid to enter said chamber upon opening said first valve means, said volume also being adapted to decrease by the action of said plunger and to allow fluid to exit from said chamber upon opening said second valve means and closing said first valve means.

19. A sampling device as in claim 18 wherein said plunger is moveable between said predetermined limits by actuating means, said actuating means being operable to open and close said first and second valve means, respectively, at a predetermined interval.

20. A sampling device as in claim 19 and further including limiting means, said limiting means operable to limit the movement of said plunger defining the maximum volume of said sampling chamber.

21. A sampling device to sample fluid, said device comprising a probe adapted to extend into fluid and to act as input port, a housing connected to said probe, first and second valve means within said housing adapted to admit fluid and to allow said fluid to exit, respectively, a sampling chamber comprising a plunger moveable within a cylinder between minimum and maximum volume positions, said plunger being moveable between said minimum and maximum volume position by cam means independently of the pressure of said fluid, said cam means also being adapted to open and close said first and second valve means, respectively, at predetermined intervals, and limiting means in said sampling chamber adapted to adjustably limit the maximum volume position of said plunger.

22. A sampling device for sampling fluid, said device comprising a probe, a housing connected to said probe, a passageway extending through said probe and housing, first and second valve means and a sampling chamber in said housing adapted to receive fluid when said first valve means is opened and to allow said fluid to exit when said second valve means is opened and said first valve means is closed, and actuating means connected to said housing for a sequential operation cycle of opening and closing said first and second valve means, said actuating means including coupling means between said actuating means and said first and second valve means, said coupling means allowing manual operation of said first and second valve means without removal of said actuating means from said housing and without destruction of said sequential operation cycle.

23. A sampling device as in claim 22 wherein each of said coupling means comprises slot receptacles and a swivel link, one of said receptacles being connected to said valve means and another of said receptacles being connected to said actuating means, said swivel link being removably connected on each respective end to said slot receptacles.

24. A sampling device as in claim 23 wherein one of said respective slot receptacles contains spring means acting to exert a retention force on the first end of said swivel link in said slot receptacle opposed to the second end of said swivel link in said slot receptacle containing said spring means.

25. A sampling device as in claim 24 wherein said spring means acts on a roll pin extending through and acting upon said first end of said swivel link, said roll pin being acted upon by a complementary longitudinal slot in said first end and wherein a roll pin extends through said second end of said swivel link and is acted upon by a second complementary slot in said slot receptacle.

26. A sampling device as in claim 25 wherein said first and second complimentary slots are of a length to allow longitudinal movement of said swivel link sufficient to allow removal of one of said roll pins from the complementary receptacle without removing said actuating means from said housing.

27. A sampling device to sample fluid, said device comprising a probe adapted to extend into said fluid to be sampled, a housing connected to said probe, first and second valve means in said housing, a sampling chamber adapted to hold a portion of said fluid when admitted, an actuating means to perform a sequential operation cycle of said first and second valve means and said sampling chamber, said actuating means being connected to each of said first and second valve means by first and second receptacles, one of said receptacles being connected to said actuating means and the other of said receptacles being connected to said respective valve means, a swivel link adapted to be inserted into each said receptacles, said swivel link having a first and second end portion, each end portion, respectively, being adapted to fit in a corresponding one of said receptacles, a roll pin extending through each respective end of said swivel link and beyond said receptacles, said roll pins being accommodated by conforming longitudinal slots in said receptacles, spring means in one of said receptacles acting to exert a retaining force on said roll pin and conforming slot in the other of said receptacles, said conforming longitudinal slots adapted to allow longitudinal movement of said swivel link within said receptacle whereby one roll pin and the corresponding end of said swivel link may be manually removed from said swivel link without removal of said actuating means from said housing for operation of said first or second valve means without destruction of said sequential operation cycle.

28. A sampling device as in claim 27 wherein said roll pin and corresponding end of said swivel link act on the end of said respective receptacle after removal and whereby upon rotation of said receptacle, said roll pin returns to a position wherein it is accommodated by said corresponding longitudinal slot in said receptacle.

29. A coupling mechanism for a sampling device, said coupling mechanism comprising first and second spaced apart receptacles rotatable about substantially the same longitudinal axis, a swivel link joining said receptacles and rotatable about substantially the same longitudinal axis, said swivel link having first and second end portions, respectively accommodated in said first and second receptacles, said first and second end portions having roll pins therein extending substantially transverse to said longitudinal axis and through respective accommodating slots in said receptacles, said slots allowing limited longitudinal movement of said roll pins and swivel link, spring means in one of said receptacles acting on said first roll pin of said respective end portion to exert a retaining force between said second roll pin and its respective accommodating slot whereby said end portion of said swivel link may be removed from said receptacle along said longitudinal axis such that said roll pin acts on the end of such receptacle and whereby upon rotation of said receptacle, said roll pin may return to its respective accommodating slot.

* * * * *